United States Patent [19]

Baier et al.

[11] Patent Number: 5,118,609

[45] Date of Patent: * Jun. 2, 1992

[54] CARRIER FLEECE FOR USE AS A REAGENT CARRIER FROM WHICH REAGENTS CAN BE DISSOLVED IN IMMUNOLOGICAL ANALYSIS

[75] Inventors: Manfred Baier, Seeshaupt; Helmut Jering, Tutzing; Rolf Lerch, Ilvesheim; Dieter Mangold, Maxdorf; Ellen Mössner; Gunter Pappert, both of Tutzing; Siegfried Nötzel, Wilhelmsfeld, all of Fed. Rep. of Germany

[73] Assignee: Boehringer Mannheim GmbH, Mannheim, Fed. Rep. of Germany

[ * ] Notice: The portion of the term of this patent subsequent to Feb. 7, 2006 has been disclaimed.

[21] Appl. No.: 648,685

[22] Filed: Jan. 31, 1991

Related U.S. Application Data

[63] Continuation of Ser. No. 296,429, Jan. 12, 1989, abandoned.

[30] Foreign Application Priority Data

Jan. 27, 1988 [DE] Fed. Rep. of Germany ....... 3802366

[51] Int. Cl.⁵ ................ G01N 33/535; G01N 33/548; C12N 11/12; C12N 11/08
[52] U.S. Cl. .................................... 435/7.9; 435/7.5; 435/174; 435/179; 435/180; 435/805; 435/970; 436/530; 436/531; 530/814; 530/815
[58] Field of Search ............... 435/4, 7.5, 7.9, 174, 435/179, 180, 805, 970; 436/530, 531; 530/814, 815

[56] References Cited

U.S. PATENT DOCUMENTS

| | | | |
|---|---|---|---|
| 4,803,171 | 2/1989 | Baier et al. | 435/805 X |
| 4,820,633 | 4/1989 | Herrmann | 436/530 X |
| 4,820,644 | 4/1989 | Schafer et al. | 436/538 X |

OTHER PUBLICATIONS

Kazu et al., Abstract Bulletin, vol. 58, No. 1, Jul. 1987, p. 137, Abstract No. 1069.
Shinoki et al., Abstract Bulletin, vol 58, No. 3, Sep. 1987, p. 410, Abstract No. 3676.

Primary Examiner—David M. Naff
Attorney, Agent, or Firm—Felfe & Lynch

[57] ABSTRACT

A carrier fleece is prepared for use as reagent carrier from which reagents can be dissolved in as assay such as immunological analysis. The carrier fleece contains from 5 to 60% by weight of cellulose-containing fibers, from 40 to 95% by weight of polyester or polyamide polymer fibers or a combination thereof and from 5 to 30% by weight of the fibers of an organic binding agent which has a hydroxyl or an ester group or a combination thereof. In an immunological analysis, the carrier fleece is impregnated with an immunologically active agent such as a beta-galactosidase conjugate and then introduced into a solution of a sample containing an immunologically active substance to be analyzed. The immunologically active agent is eluted into the sample solution and the presence of the immunologically active substance in the sample is determined.

10 Claims, No Drawings

CARRIER FLEECE FOR USE AS A REAGENT CARRIER FROM WHICH REAGENTS CAN BE DISSOLVED IN IMMUNOLOGICAL ANALYSIS

This is a continuation of application Ser. No. 296,429 filed on Jan. 12, 1989 now abandoned.

The present invention is concerned with a carrier fleece for dissolvably impregnated reagents.

In clinical diagnosis, as well as in the analysis of foodstuffs, essential articles and water, many parameters are frequently determined. For this purpose, detection processes are often carried out with the use of enzymes or of detection processes according to the immunoassay principle with the use of immunologically active substances. Already prepared test kits which contain all of the components required for analysis are commercially available for these determinations which have to be continually carried out. In the simplest form, the individual components are thereby present as solutions which are then easy and quick to measure. Especially in the case of automatic analysers, which are increasingly used in large laboratories for routine diagnosis, determination processes are to be carried out the most simply with the use of reagents in solution.

However, many substances, especially biologically active molecules, are not stable in solution and can, therefore, not be stored in this form for comparatively long periods of time. Therefore, these substances are used either in the form of tablets in which, however, problems arise since they are either pressed too hard and are then difficult to dissolve or they do not have a sufficiently great hardness and, therefore, crumble so that the dosing is inexact.

Furthermore, it is known to use lyophilisates which, for use in the test, are reconstituted by the addition of a solvent, which is usually water. However, a disadvantage of lyophilisates is the process for the preparation thereof which is very laborious and expensive.

In order to avoid these disadvantages, it has already been suggested to impregnate paper fleece with reagents and then to introduce the paper fleece into the reaction solution during the determination process. For this purpose, the reagent must, on the one hand, adhere very well to the paper fleece in order that, due to premature dissolving off, the amount which is impregnated into the fleece is not changed. On the other hand, it is necessary that, in the case of introduction into the reaction solution, the applied reagent is rapidly and completely eluted. The previously known paper fleeces are still not satisfactory since they either bind the applied reagent to too small an extent so that even during storage a part of the applied reagent dissolves off or the binding of the reagent is too strong so that it cannot be eluted quickly and completely.

Furthermore, for biologically active materials, there is, in addition, the problem of stability. Enzymes and immunologically active substances in particular lose their activity in the case of comparatively long storage, which has a disadvantageous effect on the detection processes for which they are used.

It is an object of the present invention to provide a carrier fleece with which reagents, especially conjugates of haptens, antigens and antibodies with labelling substances and protein conjugates, can be dissolvably impregnated. These carrier fleeces are to bind the reagents in such a manner that no loss of activity takes place. Neither enzymes which are impregnated as such or as conjugates nor biologically active substances are to lose their activity due to drying and storage. Upon dipping into the sample solution, the conjugate is to be eluted easily and completely. Furthermore, it is important that the carrier fleece per unit surface area takes up a definitely reproducible amount of the reagent. In addition, the carrier fleece must be such that it can be mechanically divided up not only in a wet state but also in a dry state. In addition, it must not tear either in the wet state or in the dry state. Furthermore, the carrier fleece is to stabilise the reagent in such a manner that no loss of activity takes place, even in the case of comparatively long storage.

Thus, according to the present invention, there is provided a carrier fleece for dissolvable impregnated reagents, wherein it is composed of
a) fibres based on cellulose,
b) polymer fibres based on polyester and/or polyamide and
c) an organic binding agent which has hydroxyl and/or ester groups.

Surprisingly, we have found that a fleece which has the above composition fulfills all the mentioned requirements. It leads to a stabilisation of the reagents so that even after comparatively long storage no loss of activity occurs. Furthermore, the carrier fleece can be mechanically divided up very well and does not tear either in a wet or dry state. In the case of storage, the applied reagent does not dissolve off but, in the case of immersion in the sample solution, is immediately and completely eluted. A nonspecific binding of substances present in the sample solution does not occur.

In order to achieve these advantageous properties, the carrier fleece must consist of three components. The first component is fibres based on cellulose. For this purpose, there can be used all known fibres which consist preponderantly of cellulose. As cellulose fibres, there are preferably used regenerated cellulose, cellulose pulp and linters. As regenerated cellulose, there is designated a material which is obtained by the alkalisation of cellulose to give alkali metal cellulose, subsequent treatment with carbon disulphide with the formation of cellulose xanthates, dissolving the cellulose xanthates in an aqueous solution of an alkali metal hydroxide and spinning to give viscose filaments. Cellulose pulp can be obtained by a complete chemical digestion of cellulose-containing materials and subsequent bleaching. As linters there are designated short, non-spinnable cotton fibres which are obtained from cotton seeds.

In a preferred embodiment of the carrier fleece according to the present invention, there is used a mixture of regenerated cellulose and linters, preferably in a ratio of 5 to 1:1.

The second component are polymer fibres based on polyester and/or polyamide. There can thereby be used pure polyester and/or polyamide fibres, as well as mixed fibres.

As polyamides, there are especially preferably used those with a specific weight of from 1.14 to 1.15 g./cm$^3$, a length of cut of 4 to 6 mm. and a fibre fineness of 2.2 dtex.

Especially preferred polyester fibres are fibres with a specific weight of about 1.17 g./cm$^3$, a length of cut of 3 to 6 mm. and a fibre fineness of 1.7 to 3.3 dtex.

The cellulose and polymer fibres preferably have a fibre fineness of 1.7 to 4.5 Detex and have a length of 3 to 12 mm.

As further important component, the carrier fleece according to the present invention contains an organic binding agent which has hydroxyl and/or ester groups. For this purpose, there are preferably used polyvinyl alcohol and polyacrylic acid esters.

The polyvinyl alcohol is preferably used as fibre material with a length of cut of 4 mm. and a specific weight of 1.26 to 1.30 g./cm$^3$. The acrylic acid ester is a non-ionic, self cross-linking acrylic resin dispersion.

From these three components and water, a carrier fleece is produced on an inclined sieve machine according to the usual processes used for the manufacture of paper. No further additives and adjuvants are necessary.

The three components essential for the present invention can be varied within wide limits. The carrier fleece according to the present invention is preferably composed of 5 to 60% by weight cellulose-containing fibres and 40 to 95% by weight of polymer fibres and contains, referred to the weight of the fibre components, 5 to 30% by weight of binding agent. If polyester fibres are used as polymer fibres, then the proportion of polymer fibres is preferably in the upper range, i.e. 60 to 95%. If polyamide fibres are used as polymer fibres, then the proportion of polymer fibres is preferably in the lower range, especially from 40 to 60%.

The carrier fleece according to the present invention is very well suited for impregnation with reagents for immunological determinations. Therefore, a further subject of the present invention is the use of the carrier fleece according to the present invention for the dissolvable impregnation with reagents for immunological determinations, for example haptens, antigens, antibodies and/or fragments thereof, as well as conjugates of these immunologically active substances with labelling substances, and also synthetic peptides. The carrier fleece according to the present invention can also be used for the dissolvable impregnation with other binding components, for example biotin/avidin/streptavidin, protein A/IgG and concanavalin A/mannose.

The carrier fleeces according to the present invention are preferably used for the dissolvable impregnation with conjugates of immunologically active substances and labelling substances, for example enzymes. Especially preferably, they are used for the dissolvable impregnation with β-galactosidase conjugates.

Surprisingly, we have found that an excellent stability of the impregnated reagents can be achieved with the carrier fleece according to the present invention. This is particularly surprising since the individual components of the carrier fleece according to the present invention are not able to bring about this stabilisation.

The following Examples are given for the purpose of illustrating the present invention. Unless otherwise stated, the parts are parts by weight:

EXAMPLE 1

A carrier fleece was produced which consisted of 80 parts of polyester fibres with a fibre fineness of 3.3 dtex and a fibre length of 4 mm, 20 parts of regenerated cellulose with a fibre fineness of 1.7 dtex and a length of cut of 3 mm., as well as 20 parts of polyvinyl alcohol fibres with a length of cut of 4 mm. The fibre materials, i.e. polyester, regenerated cellulose and polyvinyl alcohol, were slurried with water at a material density of 0.3% in mixing vats or individually.

The fibre material was subsequently pumped to a rotating sieve. While the fibre mixture was freed from water or the water was sucked off by a vacuum, the fibres orientate on the upper side of the sieve and were contact dried as fleece with a dry content of about 20% over drying cylinders.

EXAMPLE 2

In the manner described in Example 1, a carrier fleece was produced which had the following composition:
polyamide: fibre fineness 2.2 dtex/length of cut 6 mm.; 40%
regenerated cellulose: fibre fineness 1.7 dtex/length of cut 3 mm.; 30%
linters: 20%
polyvinyl alcohol: length of cut 4 mm.; 10%

EXAMPLE 3

Various carrier fleeces were produced and impregnated with a conjugate of polyclonal sheep anti-digoxin-antibody-Fab fragments and β-galactosidase (PAB<Dig>S-Fab(IS)-β-Gal). The carrier fleeces were impregnated in such a manner that each carrier fleece had an enzyme activity of 1249 mE. These carrier fleeces were introduced into an aqueous solution and the activity which passed into the solution determined. The corresponding amount of conjugate was dissolved in 20 μl. 100 mMole/liter Hepes (pH 7.25)+1.5% polyethylene glycol (PEG 6000) and a fleece (6×8.4 mm.) impregnated with this solution. For this purpose, the fleece was strung up with metal needles and immediately after the impregnation was dried for 30 minutes at 35° C. in a circulating air drying cabinet, subsequently immediately introduced into drying tubes and stored overnight at 4° C. The so impregnated carrier fleeces each displayed an enzyme activity of 1249 mE. For the determination of the elutability, the fleeces were eluted with 1 ml. incubation buffer (110 mMole/liter Hepes (pH 7.25), 0.9% sodium chloride, 2 mMole/liter magnesium aspartate, 0.1% bovine serum albumin and 0.2% Tween (polyoxyethylene sorbitan carboxylic acid ester). Thereafter, the enzyme activity which had passed into solution was determined. The evaluation took place via a calibration curve. The composition of the individual fleeces as well as the results obtained, are set out in the following Table 1:

TABLE 1

| fleece type | activity used (in mE) | activity eluted (in mE) | non-specific binding (in %) |
|---|---|---|---|
| 40 parts polyamide<br>30 parts regenerated cellulose<br>20 parts linters<br>10 parts polyvinyl alcohol | 1249 | 1151 | 8 |
| 90 parts polyester<br>10 parts regenerated cellulose<br>20 parts acrylic acid ester | 1249 | 1257 | 1 |
| 80 parts polyester<br>20 parts regenerated cellulose<br>20 parts polyvinyl alcohol | 1249 | 1237 | 1 |

EXAMPLE 4

Carrier fleeces according to the present invention, the compositions of which are given in the following Table 2, were impregnated with a solution which had the following composition:
50±0.2 mMole/liter Hepes (pH 7.25)
1±0.05% Crotein C
5±0.2 mMole/liter magnesium aspartate
200 U/liter PAB<Dig>-S-Fab(IS)-β-Gal as lyophilisate.

The carrier fleeces thus impregnated were tested for their stability. They were stored for 3 weeks at 35° C. with 2% moisture. As reference, fleeces were used which had been stored at +4° C. and 2% moisture in a refrigerator, as well as non-stressed paper fleeces. For the determination of the activity, there was determined the enzymatic activity (EA), after elution of the reagent, by the addition of 5 mMole/liter chlorophenol red-β-D-galactoside (prepared according to Federal Republic of Germany patent specification No. 33 45 748) in water in which the extinction increase was monitored at 578 nm.

The immunological activity (IA) was also determined. For this purpose, to the eluted immunological reagent was added a human serum dilute 1:5 which contained a definite amount of digoxin (0 to 5 ng./ml.). Incubation was carried out for 5 minutes at 37° C. and the mixture then applied to a solid phase which contained immobilised digoxin. From the solid phase, free conjugate was bound and from the supernatant the enzymatic activity could then be determined as above. The measurement signal was proportional to the amount of digoxin in the sample.

The results obtained are set out in the following Table 2:

TABLE 2

| fleece type | directly after production % activity | | 4° C./3 wks. % activity | | 35° C./3 wks. % activity | |
|---|---|---|---|---|---|---|
| | EA | IA | EA | IA | EA | IA |
| 40 parts polyamide 30 parts regenerated cellulose 20 parts linters 10 parts polyvinyl alcohol | 100 | 100 | 98 | 96 | 91 | 97 |
| 90 parts polyester 10 parts regenerated cellulose 30 parts polyacrylic acid ester | 100 | 100 | 99 | 97 | 95 | 94 |
| 80 parts polyester 20 parts regenerated cellulose 20 parts polyvinyl alcohol | 100 | 100 | 97 | 98 | 93 | 95 |

EXAMPLE 5

A fleece was produced for 90 parts polyester, 10 parts regenerated cellulose and, referred to the fibres, 30 parts polyacrylic acid ester. A conjugate was applied to this fleece. It was tested for elutability. 99% of the applied activity was found in the solution after elution.

EXAMPLE 6

A fleece was prepared from 30 parts polyamide, 20 parts linters, 30 parts regenerated cellulose and 10 parts polyvinyl alcohol. This fleece was impregnated with a solution containing an immunological conjugate and subsequently dried. The elutability was then tested. Of the applied amount of activity, 98% could be detected in the eluted solution.

What is claimed:

1. A method for carrying out an immunological analysis which comprises the steps of: providing a reagent carrier comprising a carrier fleece consisting essentially of
a) from 5 to 60% by weight of cellulose-containing fibres,
b) from 40 to 95% by weight of polymer fibres selected from the group consisting of polyester, polyamide and mixture thereof, and
c) an organic binding agent which has a hydroxyl or an ester group or a combination thereof in an amount of from 5 to 30% by weight of the fibre components, said fleece being impregnated with an immunologically active agent selected from the group consisting of haptens, antigens, antibodies, antibody fragments, and conjugates thereof with labelling substances and/or synthetic peptides, said agent being easily and substantially completely elutable into a solution of a sample containing an immunologically active substance to be analyzed; introducing said reagent carrier into a composition comprising a solvent and said sample, said solvent being a solvent for the immunologically active agent, whereby the immunologically active agent is eluted into the solution; and determining the presence or amount of the immunologically active substance which reacts with the immunologically active agent.

2. A method according to claim 1 wherein, in the carrier fleece, 60 to 40% by weight of the fibres are cellulose-containing fibres, 40 to 60% by weight of the fibres are polyamide, and the organic binding agent is polyvinyl alcohol.

3. A method according to claim 1 wherein, in the carrier fleece, 5 to 40% by weight of the fibres are cellulose-containing fibres, 60 to 95% by weight of the fibres are polyester, and the organic binding agent is polyvinyl alcohol.

4. A method according to claim 1 wherein the cellulose-containing fibres are selected from the group consisting of regenerated cellulose, linters and cellulose pulp.

5. The method of claim 4 wherein the cellulose-containing fibres consist of a mixture of regenerated cellulose and linters.

6. The method of claim 5 wherein the ratio of regenerated cellulose to linters is from 5:1 to 1:1.

7. A method according to claim 1 wherein, in the carrier fleece, the polyester fibres have a weight of about 1.17 g/cm³, a length of cut of 3 to 6 mm, and a fibre fineness of 1.7 to 3.3 dtex.

8. A method according to claim 1 wherein, in the carrier fleece, the polyamide fibres have a specific weight of 1.14 to 1.15 g/cm³, a length of cut of 4 to 6 mm, and a fibre fineness of 2.2 dtex.

9. A method according to claim 2 in which the immunologically active agent impregnated into the carrier fleece a beta-galactosidase conjugate.

10. A method according to claim 2 in which the reagent carrier additionally comprises binding components selected from the group consisting of biotin, avidin, streptavidin, protein A, IgG, concanavalin A and mannose.

* * * * *